US00PP30945P2

(12) United States Plant Patent
Flore

(10) Patent No.: US PP30,945 P2
(45) Date of Patent: Oct. 15, 2019

(54) ***PHALAENOPSIS* PLANT NAMED 'MI00863'**

(50) Latin Name: *Phalaenopsis hybrida*
Varietal Denomination: MI00863

(71) Applicant: Febe Flore, Lochristi (BE)

(72) Inventor: Febe Flore, Lochristi (BE)

(73) Assignee: Floreac N.V. div. MICROFLOR, Lochristi (BE)

( * ) Notice: Subject to any disclaimer, the term of this patent is extended or adjusted under 35 U.S.C. 154(b) by 0 days.

(21) Appl. No.: 16/350,170

(22) Filed: Oct. 10, 2018

(51) Int. Cl.
*A01H 5/02* (2018.01)
*A01H 6/62* (2018.01)

(52) U.S. Cl.
USPC ..... Plt./311
CPC ..... *A01H 6/62* (2018.05); *A01H 5/02* (2013.01)

(58) Field of Classification Search
USPC ..... Plt./311
CPC ..... A01H 5/02
See application file for complete search history.

*Primary Examiner* — Kent L Bell
(74) *Attorney, Agent, or Firm* — C. A. Whealy

(57) ABSTRACT

A new and distinct cultivar of *Phalaenopsis* plant named 'MI00863', characterized by its relatively compact and upright plant habit; moderately vigorous to vigorous growth habit; strong flowering stems; freely flowering habit with typically two racemes per plant, each inflorescence with numerous flowers; and white and purple-colored flowers with dark red purple-colored spots with white-colored "halos".

2 Drawing Sheets

Botanical designation: *Phalaenopsis hybrida.*
Cultivar denomination: 'MI00863'.

BACKGROUND OF THE INVENTION

The present invention relates to a new and distinct cultivar of *Phalaenopsis* plant, botanically known as *Phalaenopsis hybrida*, and hereinafter referred to by the name 'MI00863'.

The new *Phalaenopsis* plant is a product of a planned breeding program conducted by the Inventor in Lochristi, Belgium. The objective of the breeding program is to develop new freely flowering *Phalaenopsis* plants with good leaf shape and unique and attractive flower patterns and coloration.

The new *Phalaenopsis* plant originated from a cross-pollination in March, 2010 in Lochristi, Belgium of a proprietary selection of *Phalaenopsis hybrida* identified as code number PH01593, not patented, as the female, or seed, parent with a proprietary selection of *Phalaenopsis hybrida* identified as code number PH01225, not patented, as the male, or pollen, parent. The new *Phalaenopsis* plant was discovered and selected by the Inventor as a single flowering plant from within the progeny of the stated cross-pollination grown in a controlled greenhouse environment in Lochristi, Belgium in June, 2013.

Asexual reproduction of the new *Phalaenopsis* plant by in vitro meristem propagation in a controlled environment in Lochristi, Belgium since December, 2014 has shown that the unique features of this new *Phalaenopsis* plant are stable and reproduced true to type in successive generations.

SUMMARY OF THE INVENTION

Plants of the new *Phalaenopsis* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'MI00863'. These characteristics in combination distinguish 'MI00863' as a new and distinct *Phalaenopsis* plant:

1. Relatively compact and upright plant habit.
2. Moderately vigorous to vigorous growth habit.
3. Strong flowering stems.
4. Freely flowering habit with typically two racemes per plant, each inflorescence with numerous flowers.
5. White and purple-colored flowers with dark red purple-colored spots with white-colored "halos".

Plants of the new *Phalaenopsis* can be compared to plants of the female parent selection. Plants of the new *Phalaenopsis* differ primarily from plants of the female parent selection in the following characteristics:

1. Flowers of plants of the new *Phalaenopsis* are mostly flat whereas flowers of plants of the female parent selection are slightly undulated.
2. Flowers of plants of the new *Phalaenopsis* are white and purple in color with dark red purple-colored spots with white-colored "halos" whereas flowers of the female parent selection are white in color with dark red purple-colored spots.

Plants of the new *Phalaenopsis* can be compared to plants of the male parent selection. Plants of the new *Phalaenopsis* differ primarily from plants of the male parent selection in the following characteristics:

1. Leaves of plants of the new *Phalaenopsis* are semi-erect whereas leaves of plants of the male parent selection are horizontal.
2. Flowers of plants of the new *Phalaenopsis* are mostly flat whereas flowers of plants of the male parent selection are slightly cup-shaped.

Plants of the new *Phalaenopsis* can be compared to plants of *Phalaenopsis hybrida* 'Melody', not patented. In side-by-side comparisons, plants of the new *Phalaenopsis* differ primarily from plants of 'Melody' in the following characteristics:

1. Leaves of plants of the new *Phalaenopsis* are semi-erect whereas leaves of plants of 'Melody' are horizontal.
2. Flowers of plants of the new *Phalaenopsis* are mostly flat whereas flowers of plants of 'Melody' are slightly cup-shaped.

Plants of the new *Phalaenopsis* can also be compared to plants of *Phalaenopsis hybrida* 'Strawberry Fields', not patented. In side-by-side comparisons, plants of the new *Phalaenopsis* differ primarily from plants of 'Strawberry Fields' in the following characteristics:

1. Leaves of plants of the new *Phalaenopsis* are semi-erect whereas leaves of plants of 'Strawberry Fields' are horizontal.
2. Flowers ofplants of the new *Phalaenopsis* are broader than flowers of plants of 'Strawberry Fields'.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant. The photograph on the first sheet is a side perspective view of a typical flowering plant of 'MI00863' grown in a container. The photograph on the second sheet is a close-up view of a typical flower of 'MI00863'.

DETAILED BOTANICAL DESCRIPTION

The aforementioned photographs and following observations and measurements describe plants grown during the late summer in 12-cm containers in a glass-covered greenhouse in Lochristi, Belgium and under cultural practices typically used in commercial *Phalaenopsis* production. During the production of the plants, day and night temperatures ranged from 18° C. to 29° C. and light levels ranged from 150 Watt/$m^2$ to 375 Watt/$m^2$. Plants were 76 weeks old when the photographs and description were taken. In the following description, color references are made to The Royal Horticultural Society Colour Chart, 2015 Edition, except where general terms of ordinary dictionary significance are used.

Botanical classification: *Phalaenopsis hybrida* 'MI00863'.

Parentage:

*Female parent.*—Proprietary selection of *Phalaenopsis hybrida* identified as code number PH01593, not patented.

*Male parent.*—Proprietary selection of *Phalaenopsis hybrida* identified as code number PH01225, not patented.

Propagation:

*Type.*—By in vitro meristem propagation.

*Time to initiate roots, summer.*—About nine to ten weeks at temperatures about 26° C.

*Time to initiate roots, winter.*—About ten to eleven weeks at temperatures about 26° C.

*Time to produce a rooted young plant, summer.*—About 140 to 160 days at temperatures about 26° C.

*Time to produce a rooted young plant, winter.*—About 150 to 180 days at temperatures about 26° C.

*Root description.*—Thick, fleshy; typically grey green in color, towards the apex, close to light green; actual color of the roots is dependent on substrate composition, water quality, fertilizer, substrate temperature and age of roots.

*Rooting habit.*—Low branching; sparse.

Plant description:

*Plant form and growth habit.*—Herbaceous epiphyte; upright plant habit with typically two branched racemes per plant, each inflorescence with numerous flowers; monopodial; moderately vigorous to vigorous growth habit and moderate growth rate.

*Plant height, substrate level to top of foliar plane.*—About 17.4 cm.

*Plant height, substrate level to top of inflorescences.*—About 61.5 cm.

*Plant diameter or spread.*—About 43.5 cm.

Leaf description:

*Arrangement and quantity.*—Distichous, simple; sessile; about eight per plant.

*Length.*—About 21.9 cm.

*Width.*—About 6.4 cm.

*Aspect.*—Semi-erect.

*Shape.*—Narrowly obovate; very slightly carinate.

*Apex.*—Acute, unequal.

*Base.*—Sheathing.

*Margin.*—Entire; very slightly revolute to non-revolute.

*Texture and luster, upper and lower surfaces.*—Smooth, glabrous; slightly glossy.

*Venation pattern.*—Camptodromous.

*Color.*—Developing leaves, upper surface: Close to 143A. Developing leaves, lower surface: Close to 144A. Fully expanded leaves, upper surface: Close to NN137A; venation, close to 139A. Fully expanded leaves, lower surface: Close to between 137A and 146A; venation, close to 138A to 138B.

Inflorescence description:

*Appearance and flowering habit.*—Showy zygomorphic flowers arranged on axillary branched racemes; typically two racemes per plant; each inflorescence with about 16 flowers; flowers face outwardly on arching inflorescences supported by upright peduncles; flowers with three petals, two lateral petals and one center petal transformed into a labellum and three sepals.

*Fragrance.*—None detected.

*Time to flower.*—Plants begin flowering about 18 weeks after an inductive cooling period.

*Flower longevity.*—Long flowering period, individual flowers maintain good substance for about five months on the plant; flowers not persistent.

*Inflorescence length (lowermost flower to inflorescence apex).*—About 40.6 cm.

*Inflorescence width.*—About 26.3 cm.

*Flower buds.*—Height: About 1.8 cm. Diameter: About 1.4 cm. Shape: Broadly ovate. Color: Close to between 150A and 151D; irregularly striped and blushed with close to 182D.

*Flower diameter.*—About 9 cm.

*Flower height.*—About 8.2 cm.

*Flower depth.*—About 3.7 cm.

*Petals, quantity and arrangement.*—Three, two lateral petals and single center petal transformed into a labellum.

*Lateral petals.*—Length: About 4.4 cm. Width: About 5.3 cm. Shape: Reniform; mostly flat. Apex: Rounded. Margin: Entire. Texture and luster, upper and lower surfaces: Smooth, glabrous, velvety; matte. Color: When opening, upper surface: Proximally, close to NN155D; distally, close to N78B and N78C; margins, close to NN155D; at the base, close to 59A; spots, close to 59A; venation, close to 59A. When opening, lower surface: Proximally, close to NN155B; distally, close to N78C; margins, close to NN155D; spots, close to 59B; venation, close to 59B. Fully opened, upper surface: Proximally, close to NN155D; distally, close to N78C; towards the margins, close to 71B; margins, close to NN155D; at the base, close to 71A; spots, close to 71A; venation, close to 71A; color does not change with development. Fully opened, lower surface: Proximally, close to NN155D; distally, close to N78D; margins, close to NN155D; spots, close to 59B; venation, close to 59B.

*Labellum.*—Appearance: Tri-lobed with two lateral lobes and a central lobe. Length, lateral lobe: About 1.7 cm. Width, lateral lobes: About 1.4 cm. Length, central lobe: About 3.2 cm. Width, central lobe: About 1.8 cm. Shape, lateral lobes: Obovate. Shape, central lobe: Deltoid. Apex, lateral lobes: Rounded. Apex, central lobe: Cleft with two moderately long narrow recurved cirrose tips. Margins, lateral lobes: Entire, moderately to strongly undulate. Margins, central lobe: Entire, not undulate. Texture and luster, upper and lower surfaces: Smooth, glabrous, moderately velvety; matte. Callosities: Located at the base of the labellum and attachment point of the lateral petals; about 3.5 mm in length, about 6 mm in width and about 5 mm in height. Color: When opening, upper surface: Lateral lobes: Close to 61D; towards the base, close to 59A; white-colored band, close to N155D; towards the margins, flushed with close to 17C. Central lobe: Close to 184A; fading towards the apex to close to 59B; cirrose apices, close to 59B. Callosities: Close to 198C to 198D; towards the apex, close to N186C. When opening, lower surface: Lateral lobes: Close to 59B; fading towards the apex to close to 71A; base, close to N187D; towards the margins, flushed with close to 13B. Central lobe: Close to 61A to 61B; fading towards the apex to close to 72A; cirrose apices, close to 71A. Fully opened, upper surface: Lateral lobes: Close to 61D; fading towards the apex to close to 72B; towards the base, close to 59A; white-colored band, close to N155D; towards the margins, flushed with close to 17C. Central lobe: Close to 182A; fading towards the apex to close to 72A; cirrose apices, close to 72A. Callosities: Close to 198C to 198D; towards the apex, close to N186C. Fully opened, lower surface: Lateral lobes: Close to 59B; fading towards the apex to close to 71B; base, close to N187D; towards the margins, flushed with close to 13B. Central lobe: Close to 72B; white-colored central band, close to 155A; base, close to 182A.

*Sepals.*—Quantity and arrangement: Three, two lower lateral sepals and one upper dorsal sepal. Length, lateral sepal: About 4.6 cm. Width, lateral sepals: About 2.8 cm. Length, dorsal sepal: About 4.6 cm. Width, dorsal sepal: About 3.2 cm. Shape, lateral sepals: Ovate. Shape, dorsal sepal: Ovate to oblong. Apex, lateral sepals: Bluntly acute. Apex, dorsal sepal: Obtuse. Base, lateral and dorsal sepals: Truncate. Margin, lateral and dorsal sepals: Entire. Texture and luster, lateral and dorsal sepals, upper and lower surfaces: Smooth, glabrous, velvety; matte. Color, lateral sepals: When opening, upper surface: Close to 155C; fading towards the base to close to 145D; at the apex, close to N78B and N78C; at the base, close to 59A; margins, close to 155C; spots, close to 59A; venation, close to 59A. When opening, lower surface: Close to lighter than 146D; margins, close to 72B; spots, close to 197B; venation, close to 197B. Fully opened, upper surface: Proximally, close to NN155C; distally, close to between N78C and NN78D; base, close to 71A; margins, close to NN155C; spots, close to 59A; venation, close to N78B. Fully opened, lower surface: Proximally, close to NN155B; distally, close to N78D; margins, close to NN155B; spots, close to lighter than 183A; venation, close to lighter than 183A. Color, dorsal sepal: When opening, upper surface: Proximally, close to NN155D; distally close to N78B and N78C; margins, close to NN155D; spots, close to 59A; venation, close to 59A. When opening, lower surface: Proximally, close to 145C to 145D; margins, close to 77B to 77C. Fully opened, upper surface: Proximally, close to NN155D; distally close to N78D; margins, close to NN155D; spots, close to 59A; venation, close to N78D. Fully opened, lower surface: Proximally, close to NN155C; spots, lighter than close to 183A; margins, close to 77B to 77C; venation, close to N78B.

*Peduncles.*—Length: About 71.2 cm. Diameter: About 6 mm. Strength: Very strong. Aspect: Upright to about 45° from vertical. Texture and luster: Smooth, glabrous; matte. Color: Close to between N200B and 202A with fine dots, close to 147A.

*Pedicels.*—Length: About 4.5 cm. Diameter: About 3 mm. Strength: Moderately strong. Aspect: About 50° from peduncle axis. Texture and luster: Smooth, glabrous; matte. Color: Close to 145B; proximally, close to 197A; fading distally to close to 158D.

*Reproductive organs.*—Androecium: Column length: About 8 mm. Column width: About 6 mm. Column color: Close to N78B. Pollinia quantity: Two. Pollinia diameter (per two pollinia): About 2.5 mm. Pollinia color: Close to 23A. Gynoecium: Stigma length: About 3 mm. Stigma width: About 3 mm. Stigma shape: Reniform. Stigma color: Close to N155A. Ovary length: About 8 mm. Ovary diameter: About 1 mm. Ovary color: Close to lighter than 150D.

*Seeds and fruits.*—To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate high temperatures of about 40° C. and suitable for USDA Hardiness Zone 10.

It is claimed:

1. A new and distinct *Phalaenopsis* plant named 'MI00863' as illustrated and described.

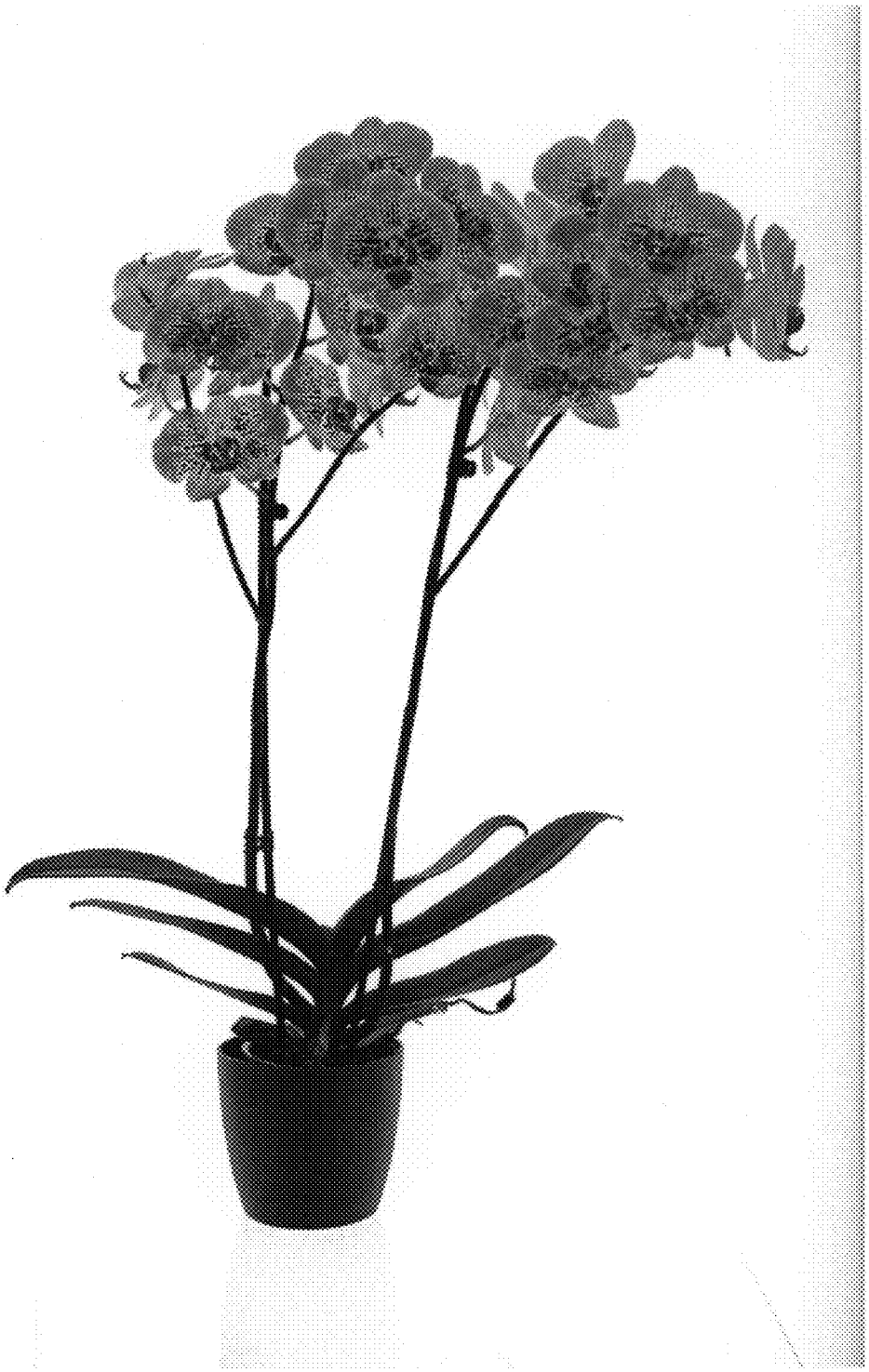

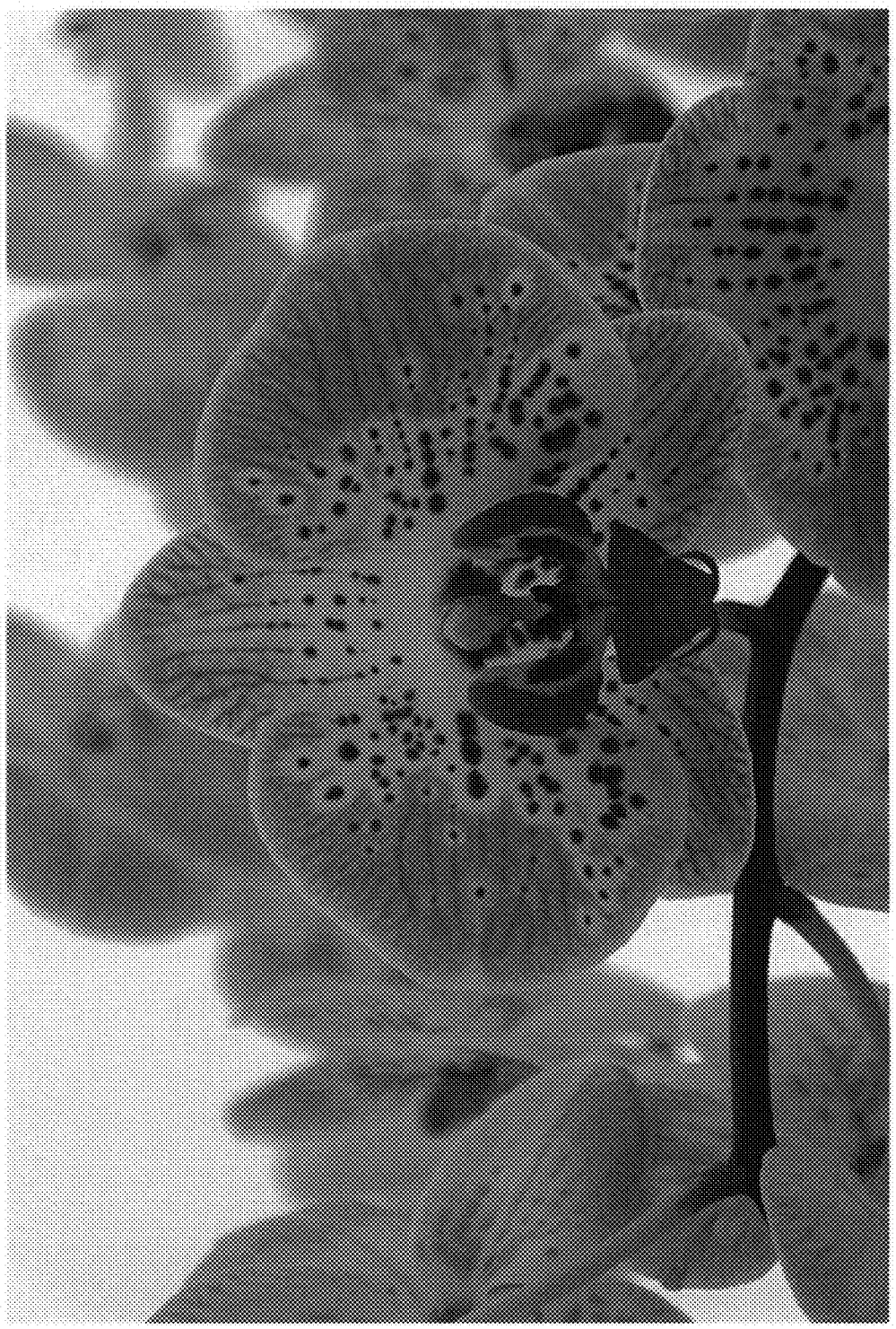

* * * * *